(12) United States Patent
Kobayashi

(10) Patent No.: US 8,851,751 B2
(45) Date of Patent: Oct. 7, 2014

(54) X-RAY IMAGING APPARATUS

(71) Applicant: Canon Kabushiki Kaisha, Tokyo (JP)

(72) Inventor: Kensuke Kobayashi, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/917,470

(22) Filed: Jun. 13, 2013

(65) Prior Publication Data

US 2013/0279662 A1     Oct. 24, 2013

Related U.S. Application Data

(63) Continuation of application No. 12/714,210, filed on Feb. 26, 2010, now Pat. No. 8,485,726.

(30) Foreign Application Priority Data

Mar. 2, 2009   (JP) ................................ 2009-047854

(51) Int. Cl.
| | |
|---|---|
| *H05G 1/64* | (2006.01) |
| *H01J 31/49* | (2006.01) |
| *H01J 31/50* | (2006.01) |
| *A61B 6/04* | (2006.01) |
| *A61B 6/00* | (2006.01) |
| *F16M 13/00* | (2006.01) |
| *F16M 11/04* | (2006.01) |
| *G03B 42/04* | (2006.01) |
| *F16M 11/10* | (2006.01) |

(52) U.S. Cl.
CPC ... *A61B 6/04* (2013.01); *A61B 6/56* (2013.01); *F16M 13/00* (2013.01); *F16M 11/04* (2013.01); *A61B 6/4233* (2013.01); *G03B 42/04* (2013.01); *F16M 11/045* (2013.01); *F16M 11/105* (2013.01); *F16M 11/10* (2013.01)
USPC ........................................ 378/189; 378/98.8

(58) Field of Classification Search
CPC ............ H05G 1/02; H05G 1/64; H01J 31/49; H01J 31/50; G21K 4/00; H01L 27/146; G01T 1/175; G01T 1/24
USPC ............. 378/19, 91, 98, 98.2, 98.8, 189–192, 378/204, 210; 250/370.01, 370.08, 370.09, 250/371, 491.1, 526; 439/1, 10, 11, 13, 439/18–24, 32, 162, 164, 374, 378–380, 439/883–894
See application file for complete search history.

(56) References Cited

U.S. PATENT DOCUMENTS

| | | | | |
|---|---|---|---|---|
| 5,130,751 | A | * | 7/1992 | Sato et al. ....................... 399/96 |
| 6,281,506 | B1 | * | 8/2001 | Fujita et al. ............... 250/370.09 |
| 6,428,206 | B1 | * | 8/2002 | Watanabe ..................... 378/197 |
| 7,549,798 | B2 | * | 6/2009 | Watanabe ..................... 378/189 |
| 7,997,796 | B2 | * | 8/2011 | De Godzinsky .............. 378/191 |
| 7,997,798 | B2 | * | 8/2011 | Liu et al. ....................... 378/198 |

FOREIGN PATENT DOCUMENTS

| | | |
|---|---|---|
| JP | 01126086 U | 8/1989 |
| JP | 11195471 A | 7/1999 |

(Continued)

*Primary Examiner* — Anastasia Midkiff
(74) *Attorney, Agent, or Firm* — Canon USA Inc. IP Division

(57) ABSTRACT

An X-ray imaging apparatus includes an imaging unit having an imaging unit power feeding mechanism configured to receive electric power from an external device; a pedestal including a pedestal power feeding mechanism configured to feed the electric power to the imaging unit; and a holder configured to position and hold the imaging unit so that a position of the imaging unit power feeding mechanism coincides with a position of the pedestal power feeding mechanism even if the imaging unit power feeding mechanism is moved with respect to the pedestal power feeding mechanism within a predetermined imaging plane.

17 Claims, 13 Drawing Sheets

(56) References Cited

FOREIGN PATENT DOCUMENTS

| | | | |
|---|---|---|---|
| JP | 11226001 A | 8/1999 | |
| JP | 2000347330 A | 12/2000 | |
| JP | 2005087255 A | 4/2005 | |
| JP | 2007010848 A | 1/2007 | |
| JP | 2008029644 A | 2/2008 | |
| JP | 2009011466 A | 1/2009 | |

* cited by examiner

X-RAY IMAGING APPARATUS

This application is a Continuation of co-pending U.S. patent application Ser. No. 12/714,210 filed Feb. 26, 2010, which claims foreign priority under 35 U.S.C. §119 from Japanese Patent Application No. 2009-047854 filed Mar. 2, 2009. The contents of the above-named applications are hereby incorporated by reference herein in their entirety.

BACKGROUND OF THE INVENTION

1. Field of the Invention

The present invention relates to an X-ray imaging apparatus including a transportable electronic cassette and a pedestal for supporting the transportable electronic cassette.

2. Description of the Related Art

In the field of medical imaging services or other imaging industries, X-ray photography has become widely used. In X-ray photography, an object is subjected to X-ray radiation, and thereafter an intensity distribution of X-rays transmitted through the object is detected in order to obtain an X-ray image of the object.

An example of a method for obtaining the X-ray image includes a film screen method. In the film screen method visible light emitted from a rare-earth phosphor, for example, which is sensitive to the X-ray, is photographed by a photographic sensitive film, and the photographic sensitive film is chemically developed to visualize the photographed visible light as the X-ray image.

Subsequent technical innovation has yielded various other methods to obtain the X-ray image. As one of the methods, there is a Computed Radiography (CR) method in which the above-described visualizing method of the film screen method is combined with digital technology in order to visualize the light. In the CR method, a latent image once stored in a fluorescent material is excited by laser light or the like and recorded as a visualized image by photoelectrically reading the latent image. The CR method requires an image reading processing and an image reading apparatus in addition to an imaging unit.

Another method for obtaining an X-ray image takes advantage of advances in semiconductor technology. More specifically, a Flat Panel Detector (FPD) has been developed using a flat sensor in which pixels, each including a minute photoelectric converter and a switching element, are arranged in a grid pattern. An advantage of the FPD is that a stable X-ray image can be obtained even if an X-ray exposure amount varies because the FPD has an extremely wide dynamic range. Another advantage of the FPD is that the X-ray image can be obtained in a time efficient manner without chemical processing. In comparison, the conventional photographic sensitive film must be transported and later developed chemically, which takes much longer processing times.

A conventional X-ray imaging apparatus is broadly divided into, according to the environment of use, a stationary cassette, which is disposed at a predetermined place such as a general imaging studio, and a transportable cassette, which can be freely transported. The FPD system also includes a transportable electronic cassette. However, as is similar to a case of the conventional film cassette, the transportable electronic cassette is required to be thin and light, to be attached to various kinds of pedestal, and to have a degree of freedom to be used in a plurality of photographing environments.

Generally, the electronic cassette uses a semiconductor sensor in a process of acquiring and outputting the X-ray image. To that end, the electronic cassette needs electric power for powering relevant modules such as the semiconductor sensor. The electronic cassette thus has a cable attached thereto for receiving power and controlling the relevant modules thereof from an external device.

However, handling the electronic cassette having the cable attached thereto is difficult because the cable used to deliver the necessary electric power may interfere with surrounding devices and prevent optimal positioning of the electronic cassette. Therefore, it is difficult for the electronic cassette with the cable to have the degree of freedom equal to that of the above described film cassette. In view of the above, a wireless electronic cassette is recently proposed, which can perform wireless communication with a photographing system control unit. The wireless electronic cassette includes a battery for supplying electric power instead of the cable.

In the wireless electronic cassette to which the electric power is supplied from the battery, a charged amount of the battery may limit a usable time period of the electronic cassette. As a result, a frequent change of the battery or a frequent charge of the electronic cassette by being connected to an external power feeding device may be required. Thus, a wireless electronic cassette powered by a battery may have difficulty in satisfying a demand that the electronic cassette be applied to a wide variety of photographing environments.

In view of the above, if the photographing is to be performed continuously and for a long period of time so that a plurality of image frames are obtained, it is desirable that the photographing be performed while the power is being supplied to the imaging unit through the external device.

Japanese Patent Laid-open No. 2005-006979 discusses a system in which a power feeding path of the battery or the external power source, or a wired or a wireless communication method is controlled according to a detection result of whether or not a cable is connected to the imaging unit. Further, in the imaging unit is provided with an electrode on an external surface, the electric power is fed from the external unit to the imaging unit through the electrode. In this arrangement, the imaging unit can be disposed in a direction the imaging unit matches to a position of a power feeding mechanism with ease by providing the power feeding mechanism to a holder, which position is securely fixed.

As described above, an X-ray imaging unit can be applied to variety of photographing environments. However, when photographing is performed with the imaging unit attached to a pedestal or the like, the imaging unit is not always positioned in a predetermined direction. Instead, the imaging unit is preferably moved to a desired position or in a desired direction. As a result, an applicable range of the imaging unit in photographing becomes remarkably wider. For example, in a case of the imaging unit having a rectangular imaging area, a diagonal direction of the imaging unit is matched to a longitudinal direction of the imaging area by moving the imaging unit to a desired position or in a desired direction, so that a wider range of photographing can be realized in one photographing event.

SUMMARY OF THE INVENTION

According to an aspect of the present invention, an X-ray imaging apparatus includes an imaging unit having an imaging unit power feeding mechanism configured to receive electric power from an external device, a pedestal including a pedestal power feeding mechanism configured to feed the electric power to the imaging unit, and a holder configured to position and hold the imaging unit so that a position of the imaging unit power feeding mechanism coincides with a position of the pedestal power feeding mechanism. In one embodiment, the holder includes a guiding portion configured to enable a translation movement of the holder to a position within a plane that is in parallel with an imaging plane of the imaging unit. In another embodiment, the holder includes a guiding portion configured to enable a rotation of the holder to an angle with respect to an axis vertical to the imaging plane. In other embodiments, the guiding portion of the holder may enable both translation and rotation of the holder with respect to the imaging plane. The holder further includes a power feeding port configured to, in a state where the imaging unit is combined with the holder, enable the imaging unit power feeding mechanism to receive the electric power even if the imaging unit power feeding mechanism and the pedestal power feeding mechanism are moved with respect to each other.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1:
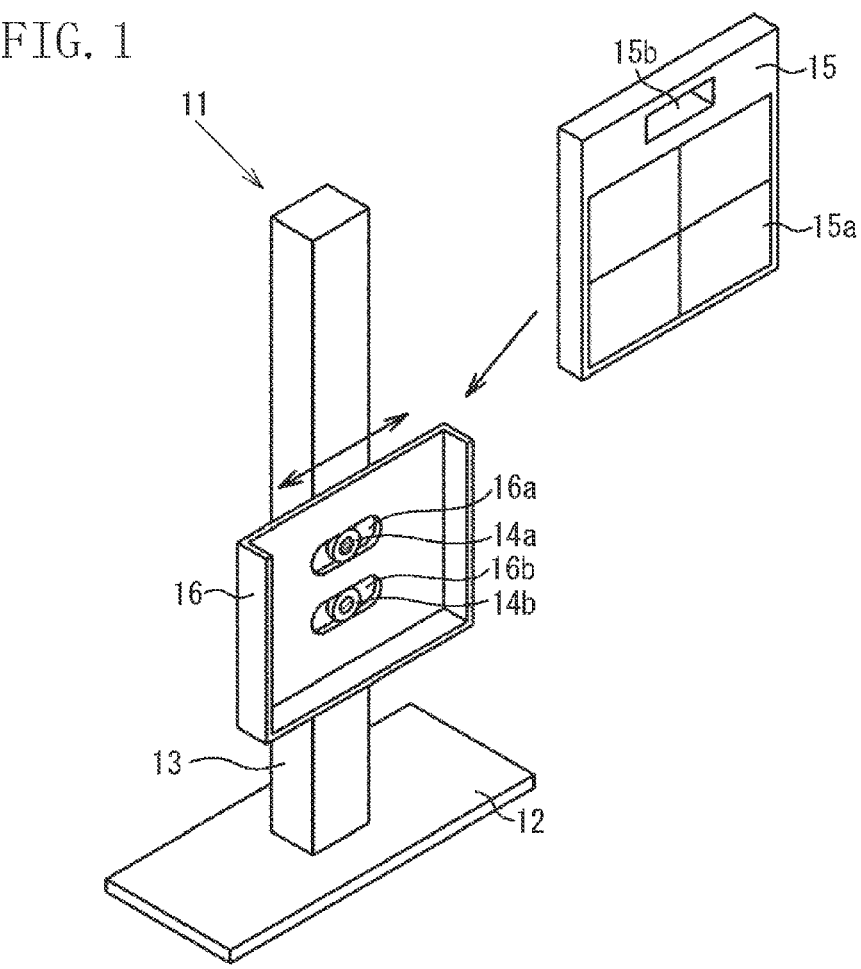
FIG. 1 is a perspective view of a pedestal according to a first exemplary embodiment.

FIG. 1 is a perspective view of a pedestal that holds an imaging unit. In a pedestal 11, a supporting post 13 is fixed to stand on a support plate 12. The supporting post 13 is provided with two cylindrical electrode construction members 14a and 14b, and further provided with a holder 16 that holds an imaging unit 15 (wireless electronic cassette). The holder 16 includes two long holes 16a and 16b configured to engage with the two cylindrical electrode construction members 14a and 14b, respectively, so that the holder 16 can be freely movable with respect to the supporting post 13. Accordingly, the two long holes 16a and 16b of the holder 16 collectively serve as a guiding portion and as a power feeding port. In this embodiment, the holder 16 is attached to the supporting post 13 in such a manner that the holder can move in translation in a horizontal direction along the electrode construction members 14a and 14b via the long holes 16a and 16b. However, in other embodiments, the holder 16 may move in translation in a vertical or other direction.

Figure 2:
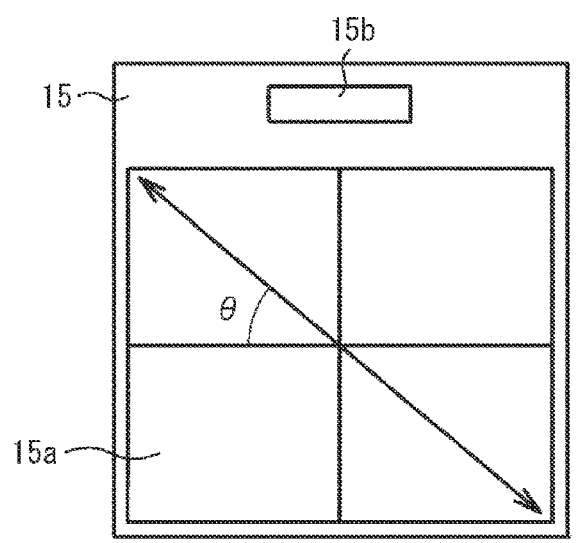
FIG. 2 is a front elevation of an imaging unit according to the first exemplary embodiment.
Figure 3:
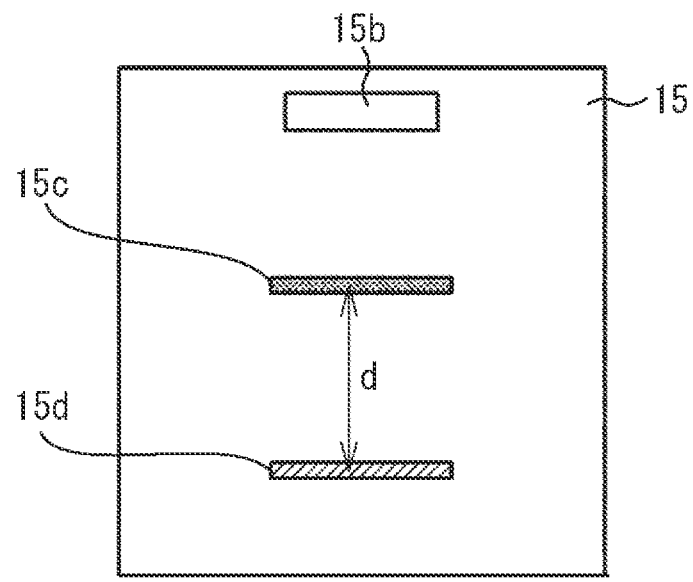
FIG. 3 is a rear elevation of the imaging unit according to the first exemplary embodiment.

FIG. 2 is a front elevation of the imaging unit 15 and FIG. 3 is a rear elevation of the imaging unit 15, respectively. The imaging unit 15 includes a rectangular X-ray irradiation surface 15a. A line that extends diagonally between two corners of the rectangular X-ray irradiation surface 15a forms an angle θ with respect to a longer side of the rectangular X-ray irradiation surface 15a. Further, an upper edge of the imaging unit 15 is provided with a holding portion 15b, and a rear surface of the imaging unit 15 is provided with linear shaped electrodes 15c and 15d. The linear shaped electrodes 15c and 15d provided in the rear surface of imaging unit 15 are separated from each other by a distance d. In operation, the linear shaped electrodes 15c and 15d are kept substantially parallel to each other, so as to maintain electrical contact with external power feeding electrodes. Accordingly, the linear shaped electrodes 15c and 15d serve as a first power feeding mechanism for the imaging unit 15 (an imaging unit power feeding mechanism). That is, power can be fed to the imaging unit 15 via the two linear-shaped electrodes 15c and 15d from an external device (not shown) through the pedestal 11. The thus fed electric power can then be stored in a built-in battery (not illustrated).

Figure 4:
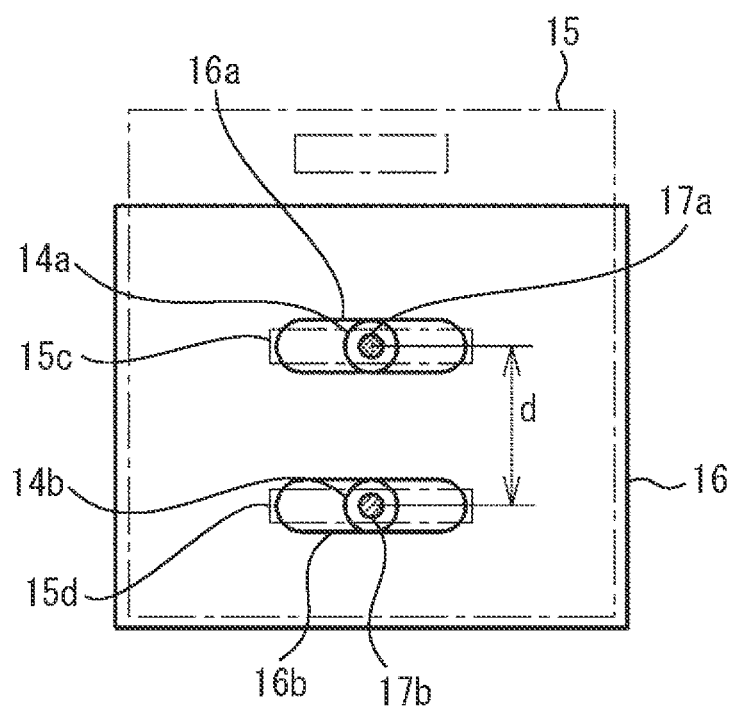
FIG. 4 illustrates a state in which the imaging unit is attached to a holder according to the first exemplary embodiment.

FIG. 4 illustrates a state in which the imaging unit 15 is attached to the holder 16 of the pedestal 11. Point-shaped electrodes 17a and 17b, which are disposed to contact with the linear shaped electrodes 15c and 15d of the imaging unit 15 respectively corresponding thereto, are provided in central portions of the circular electrode construction members 14a and 14b, respectively. The circular electrode construction members 14a and 14b having the point-shaped electrodes 17a and 17b in the central portions thereof are fixedly attached to the pedestal 11, and serve to deliver (feed) power to the linear shaped electrodes 15c and 15d of the imaging unit 15. Accordingly, the circular electrode construction members 14a and 14b having the point-shaped electrodes 17a and 17b in the central portions thereof collectively serve as a second power feeding mechanism (a pedestal power feeding mechanism).

When the imaging unit 15 and the holder 16 move together in translation, power is fed between the two power feeding mechanisms via the power feeding port. That is, power is continuously transferred from the point-shaped electrodes 17a and 17b to the linear shaped electrodes 15c and 15d—via the two long holes 16a and 16b—while the linear shaped electrodes 15c and 15d, and the point-shaped electrodes 17a and 17b are kept in corresponding contact with each other. Accordingly, the imaging unit 15 in combination with the holder 16 can be moved in translation in a longitudinal direction of the long holes 16a and 16b within a plane that is parallel to the imaging plane. It should be understood that the imaging unit 15 in combination with the holder 16 can be moved in translation by a predetermined distance approximately equal to the length of the long holes 16a and 16b. As a result, the imaging unit 15 advantageously enables specific photographing conditions other than the conventional photographing ones. For example, the above-described arrangement can enable the imaging unit 15 to perform photographing under especial conditions such as long length photographing or stereo photographing, in which highly precise lengthwise direction movement is required.

Further to the foregoing description, it is a matter of course that an imaging area can be moved in translation in a widthwise direction, as well as in a lengthwise direction, if arrangement of the electrodes of the imaging unit 15 and the electrodes of the holder 16 are rotated by 90 degrees, respectively.

Figure 5:
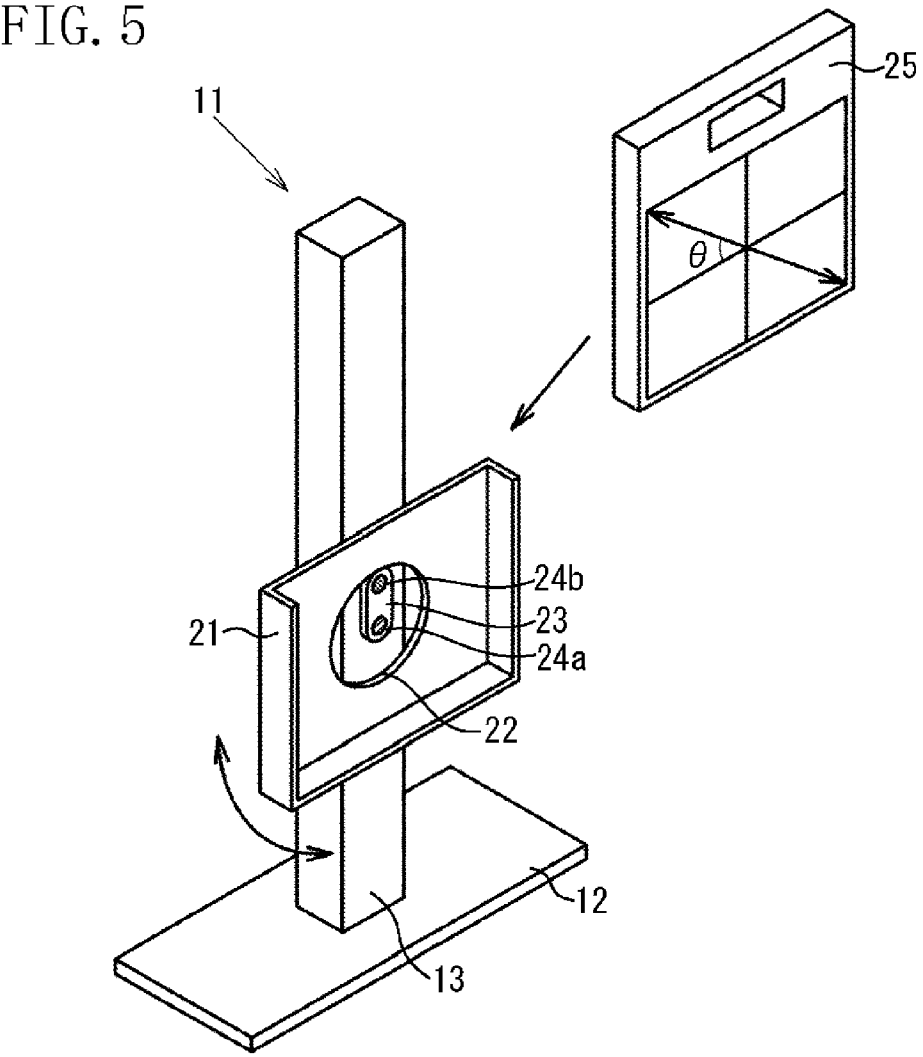
FIG. 5 is a perspective view of a pedestal according to a second exemplary embodiment.
Figure 6:
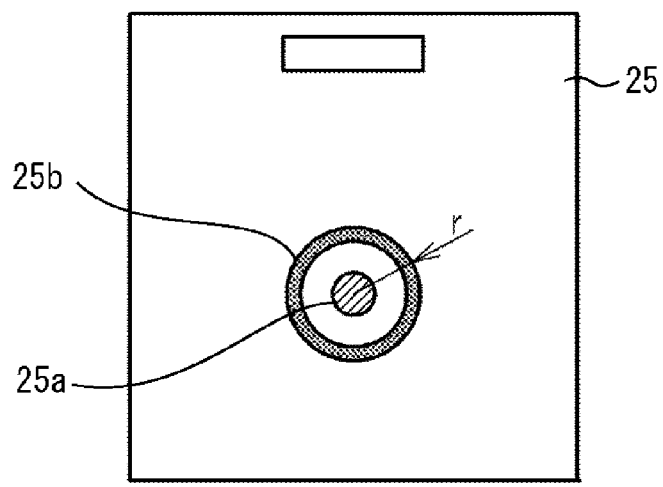
FIG. 6 is a rear elevation of an imaging unit according to the second exemplary embodiment.
Figure 7:
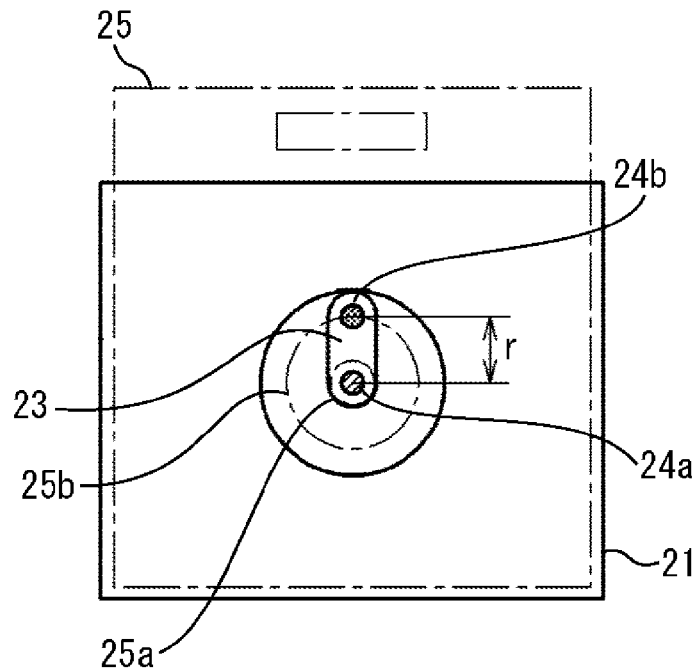
FIG. 7 illustrates a state in which the imaging unit is attached to a holder according to the second exemplary embodiment.

FIG. 5 is a perspective view of a pedestal, FIG. 6 is a rear elevation of an imaging unit, and FIG. 7 illustrates a state in which the imaging unit is attached to a holder, respectively, according to a second exemplary embodiment. Members similar to those of the first exemplary embodiment are provided with the same numbers and/or symbols and corresponding description thereof is omitted for brevity.

In the second embodiment, the supporting post 13 of the pedestal 11 is provided with a holder 21. A central portion of the holder 21 is provided with a circular hole 22 through which the holder 21 can be rotated freely. An electrode construction member 23 is attached to the supporting post 13 in a vertical direction. The electrode construction member 23 is exposed through the circular hole 22. This electrode construction member 23 is provided with point-shaped electrodes 24a and 24b, which are separated from each other by a distance r.

On a rear surface of an imaging unit 25, a point-shaped electrode 25a is formed at a position corresponding to a rotation center, and a ring-shaped electrode 25b is formed at a position of a radius r around a center of the point-shaped electrode 25a.

The imaging unit 25 is mounted into the holder 21 of the pedestal 11. Thereafter, the imaging unit 25, together with the holder 21, can be rotated by a predetermined angle with respect to an axis vertical to an imaging plane. For example, if the imaging unit 25 is rotated in a counterclockwise direction by an angle θ from an electing direction of the imaging unit 25, the diagonal line of the imaging area is oriented in a horizontal direction. Accordingly, an object that cannot fall into the longer side of the imaging area can be photographed in one shot as far as the object falls into the diagonal line of the imaging area. Therefore, the working efficiency of the imaging unit can be enhanced.

Figure 8:
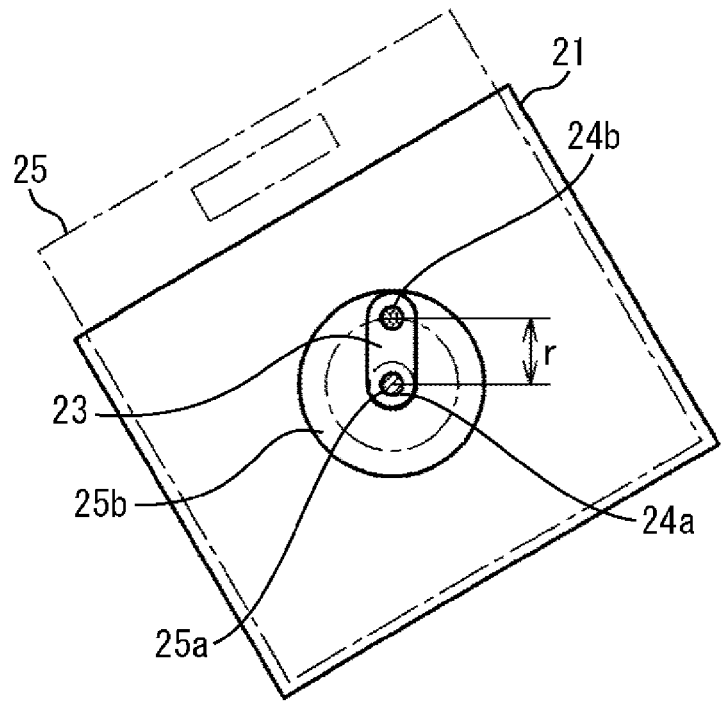
FIG. 8 illustrates a state in which the imaging unit is attached to the holder and the holder is caused to rotate together with the imaging unit according to the second exemplary embodiment.

As illustrated in FIGS. 7 and 8, a ring-shaped electrode 25b is arranged so as to coincide with a path of the point-shaped electrode 25b. Accordingly, when the imaging unit 25 rotates together with the holder 21, continuous contact between the point-shaped electrode 25a and the point-shaped electrode 24a at the center as well as a contact between the ring-shaped electrode 25b and the point-shaped electrode 24b at a distance of radius r can be kept as illustrated in FIG. 8. In this case, the different pairs of electrodes would not be overlapped or crossover to each other even if the imaging unit 25 rotates together with the holder 21 from 0 to 360 degrees.

The electrodes of the imaging unit 25 and the holder 21 of the X-ray imaging apparatus according to the second exemplary embodiment include three point-shaped electrodes 24a, 24b, and 25a, and a ring-shaped electrode 25b. Each of these structures can be easily implemented with parts having simple shapes.

Figure 9:
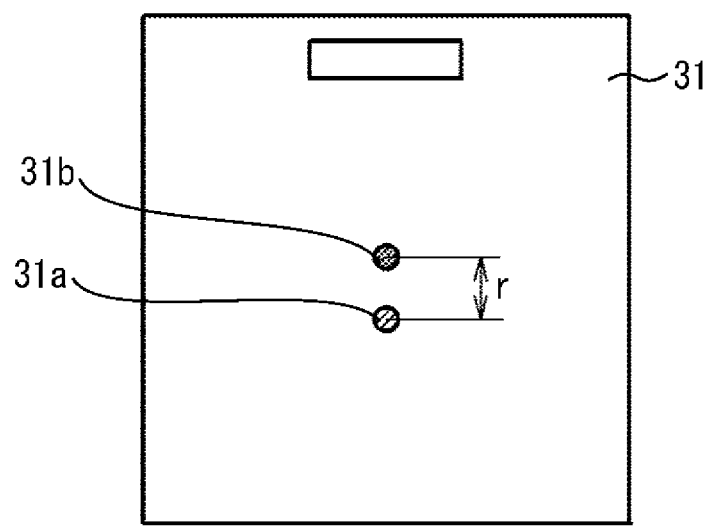
FIG. 9 is a rear elevation of an imaging unit according to a third exemplary embodiment.
Figure 10:
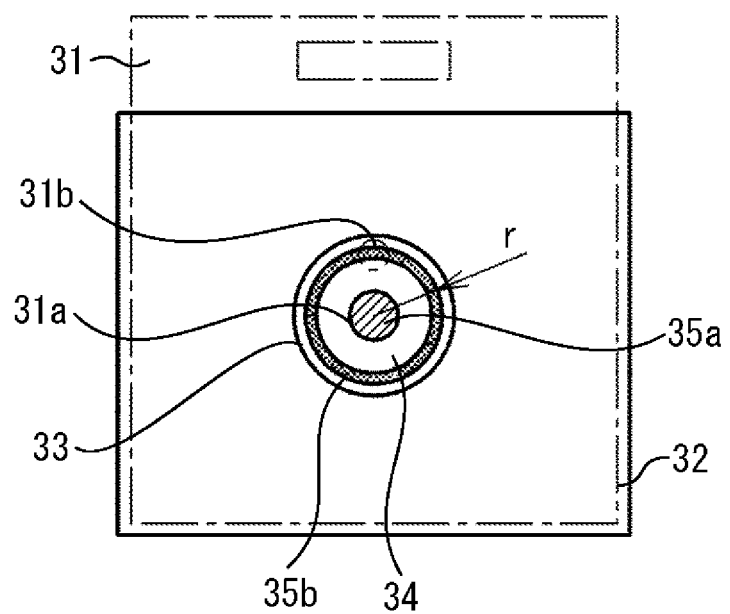
FIG. 10 illustrates a state in which the imaging unit is attached to a holder according to the third exemplary embodiment.

FIG. 9 is a rear elevation of an imaging unit, and FIG. 10 illustrates a state in which the imaging unit is attached to a holder according to a third exemplary embodiment. In the third exemplary embodiment, the electrodes to be used are interchanged between the imaging unit and the holder compared to the electrodes illustrated in the second exemplary embodiment.

More specifically, a center of a rear surface of an imaging unit 31 is provided with a point-shaped electrode 31a and a point-shaped electrode 31b is provided at a position distant from the point-shaped electrode 31a by the distance r. In the central portion of a holder 32 that is formed to be freely rotatable with respect to the supporting post, there is provided with a circular hole 33 through which an electrode construction member 34 is provided on the supporting post 13.

Figure 11:
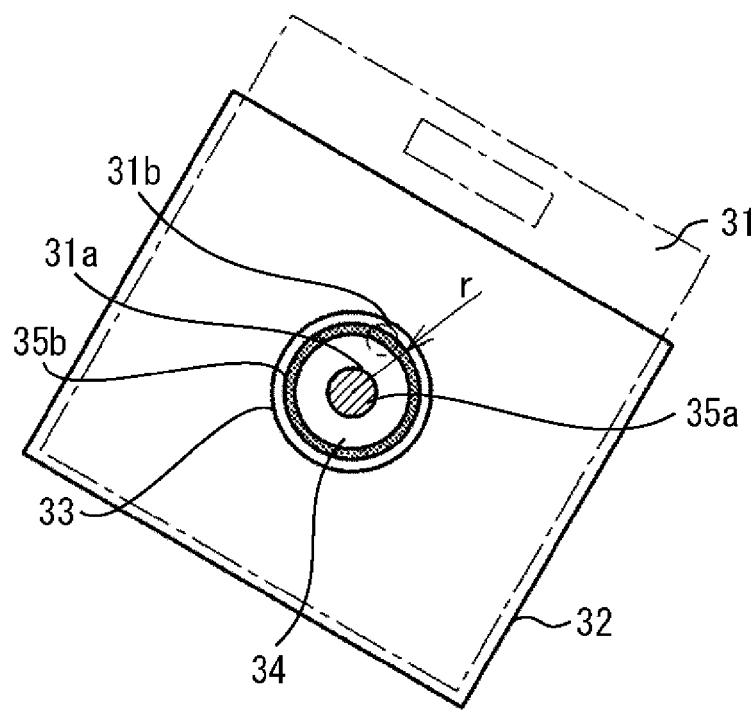
FIG. 11 illustrates a state in which the imaging unit is attached to the holder and the holder is rotated together with the imaging unit according to the third exemplary embodiment.

The electrode construction member 34 includes a point-shaped electrode 35a arranged at a rotation center and a ring-shaped electrode 35b at a position distant from the rotation center by the distance r. As illustrated in FIG. 11, when the imaging unit 31 is mounted into the holder 32 and rotated together with the holder, a contact between the point-shaped electrode 31a and the point-shaped contact 35a, and a contact between the point-shaped electrode 31b and the ring-shaped electrode 35b are kept, respectively.

An effect obtained from the X-ray imaging apparatus as a whole according to the present exemplary embodiment is almost equal to the effect obtained from the X-ray imaging apparatus according to the second exemplary embodiment. However, in the present exemplary embodiment, an area of the exposed electrodes in the imaging unit 31 can be reduced in comparison with that of the second exemplary embodiment. Therefore, when handling (e.g., carrying around) the imaging unit 31, an opportunity that the electrodes may contact with foreign materials can be reduced.

Figure 12:
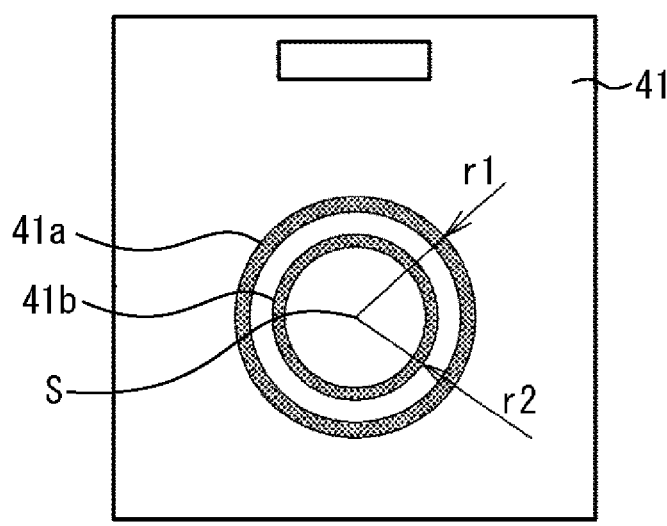
FIG. 12 is a rear elevation of an imaging unit according to a fourth exemplary embodiment.
Figure 13:
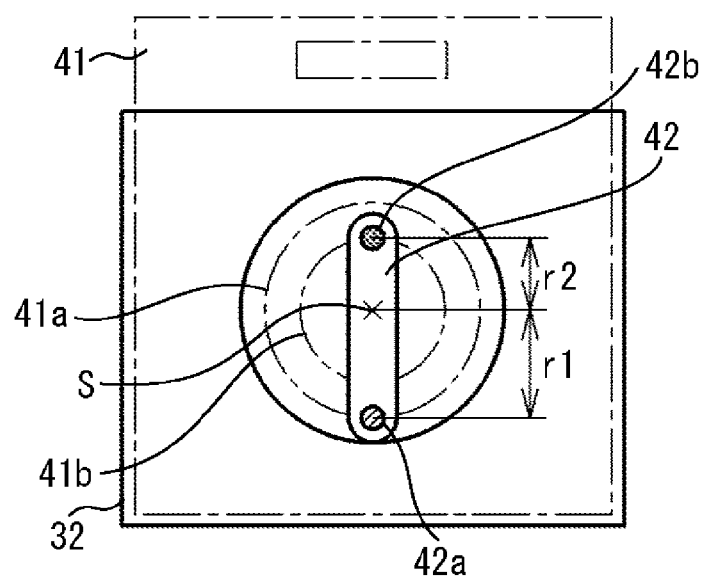
FIG. 13 illustrates a state in which the imaging unit is attached to a holder according to the fourth exemplary embodiment.

FIG. 12 is a rear elevation of an imaging unit, and FIG. 13 illustrates a state in which the imaging unit is attached to a holder according to a fourth exemplary embodiment.

A rear surface of an imaging unit 41 is provided with ring-shaped electrodes 41a and 41b at positions of radiuses r1 and r2, respectively, around the rotation center S. On the other hand, a supporting post of a pedestal (not illustrated) is provided with an electrode construction member 42. The electrode construction member 42 is provided with point-shaped electrodes 42a and 42b at positions distant from the rotation center S of a holder 32 by distances r1 and r2, respectively.

Figure 14:
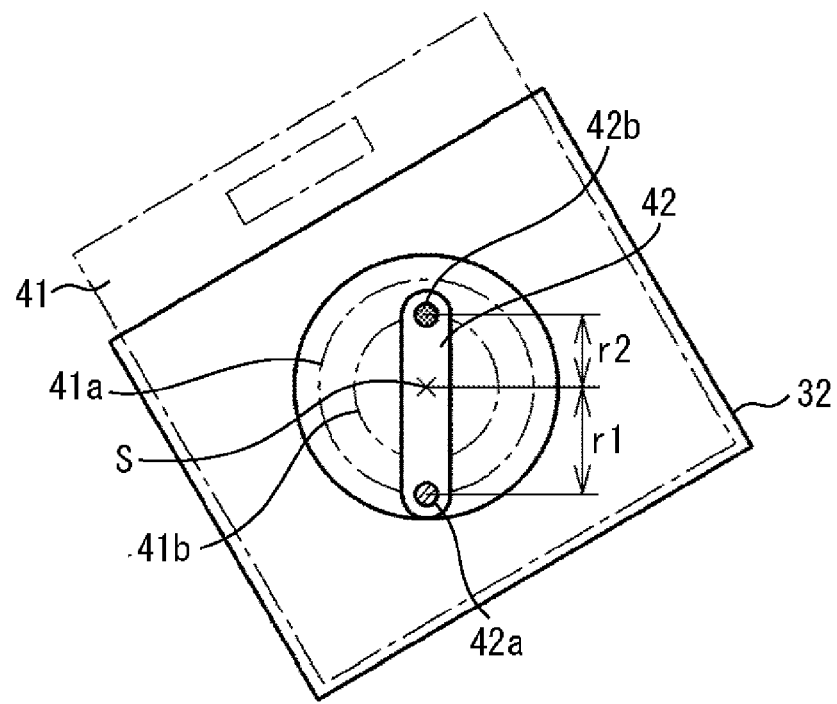
FIG. 14 illustrates a state in which the imaging unit is attached to the holder and the holder is rotated together with the imaging unit according to the fourth exemplary embodiment.

Even when the imaging unit 41 rotates together with the holder 32, continuous contact between the ring-shaped electrodes 41a and 41b positioned around the rotation center S and the corresponding point-shaped electrodes 42a and 42b can be kept, respectively, as illustrated in FIG. 14.

In an X-ray imaging apparatus according to the fourth exemplary embodiment, the imaging unit 41 can be rotated together with the holder in a similar manner as illustrated in the second and the third exemplary embodiments. Accordingly, the imaging unit 41 may be provided with only two ring-shaped electrodes 41a and 41b, and the holder 32 may be provided with only two point-shaped electrodes 42a and 42b, so that shapes of parts can be standardized.

Figure 15:
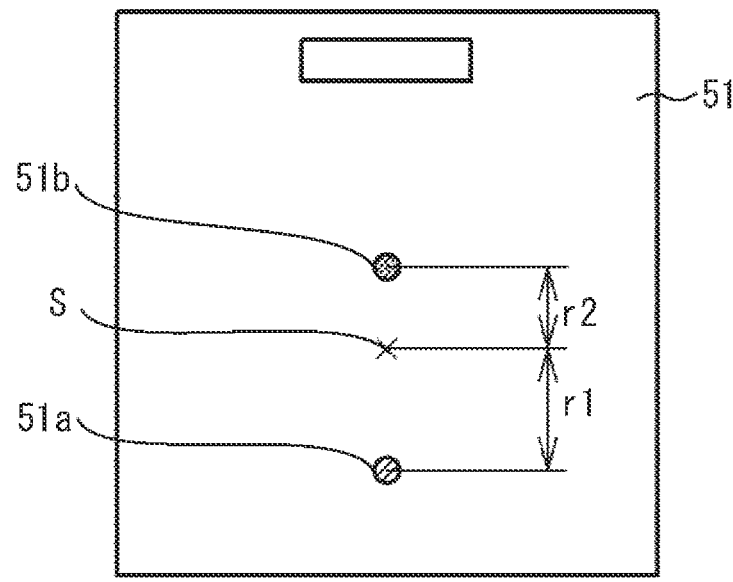
FIG. 15 is a rear elevation of an imaging unit according to a fifth exemplary embodiment.
Figure 16:
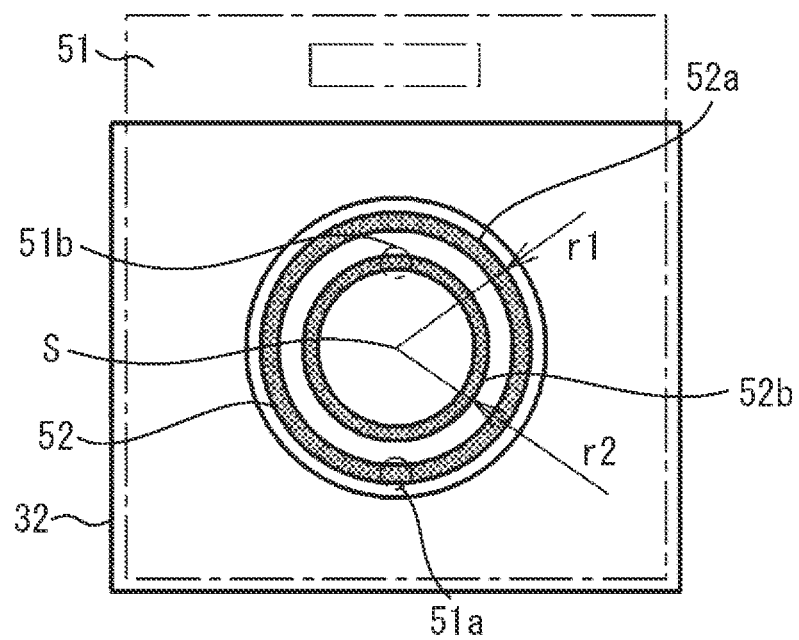
FIG. 16 illustrates a state in which the imaging unit is attached to a holder according to the fifth exemplary embodiment.

FIG. 15 is a rear elevation of an imaging unit, and FIG. 16 illustrates a state in which the imaging unit is attached to a holder according to a fifth exemplary embodiment. In the fifth exemplary embodiment, the electrodes to be used are interchanged between the imaging unit and the holder compared to the electrodes illustrated in the fourth exemplary embodiment.

A rear surface of an imaging unit 51 is provided with a point-shaped electrode 51a at a position distant from the rotation center S by the distance r1, and further provided with a point-shaped electrode 51b at a position distant from the rotation center S by the distance r2. On the other hand, a supporting post (not illustrated) is provided with an electrode construction member 52, which includes a ring-shaped electrode 52a at a position distant from the rotation center S by the distance r1 and a ring-shaped electrode 52b at a position distant from the rotation center S by the distance r2.

Figure 17:
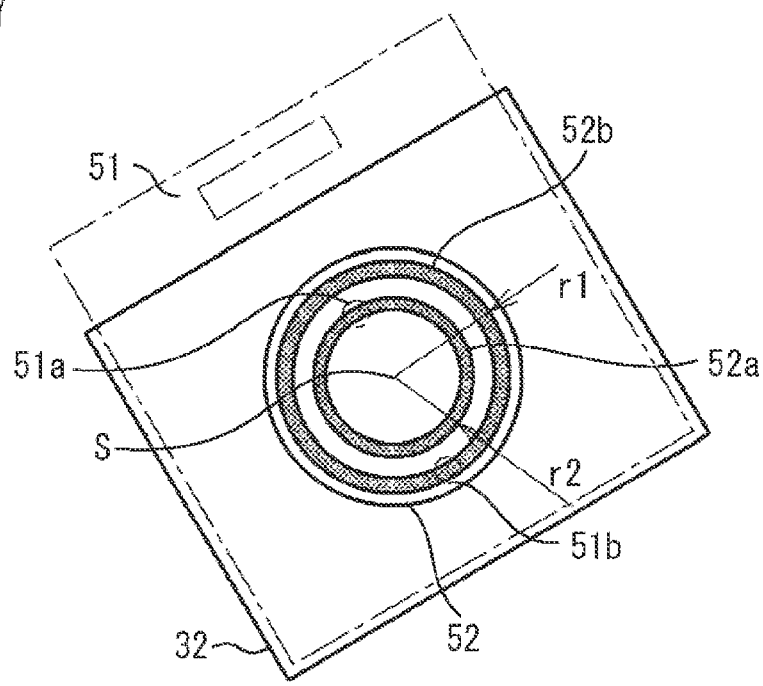
FIG. 17 illustrates a state in which the imaging unit is attached to the holder and the holder is rotated together with the imaging unit according to the fifth exemplary embodiment.

As illustrated in FIG. 17, when the imaging unit 51 is fixed to the holder 32 and thereafter is rotated together with the holder 32, constant contact between the point-shaped electrodes 51a and 51b and the corresponding ring-shaped electrodes 52a and 52b can be maintained, respectively.

An effect obtained by the X-ray imaging apparatus as a whole according to the present exemplary embodiment is almost equal to that obtained by the X-ray imaging apparatus according to the fourth exemplary embodiment. However, an area of the electrodes exposed in the imaging unit 51 can be reduced in comparison with that according to the fourth exemplary embodiment. Accordingly, when carrying the imaging unit 51, an opportunity that the electrodes may contact with the foreign materials can be even further reduced.

Figure 18:
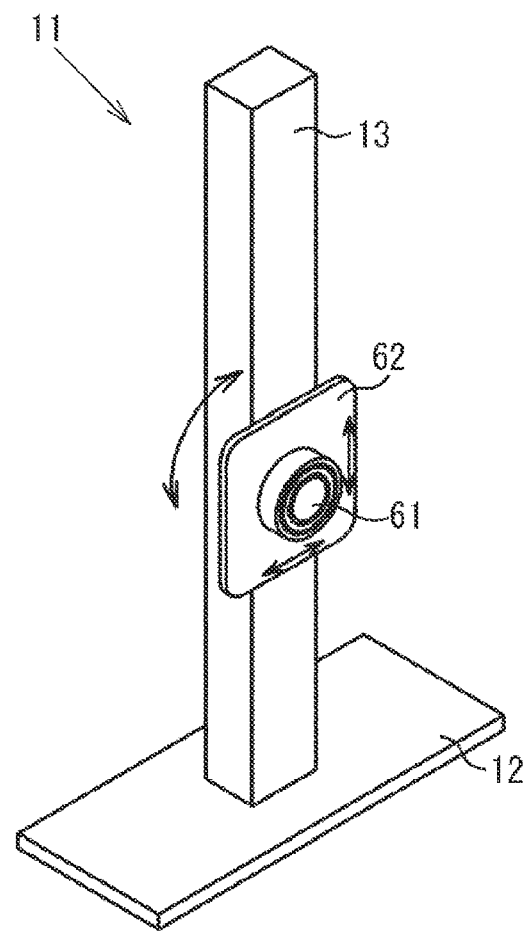
FIG. 18 is a perspective view of a pedestal according to a sixth exemplary embodiment.

FIG. 18 is a perspective view of a pedestal according to a sixth exemplary embodiment. An imaging unit and a holder are omitted to be illustrated here.

An electrode construction member 61 according to the sixth exemplary embodiment is attached to the supporting post 13 through a base plate 62. Therefore, the electrode construction member 61 is movable together with the base plate 62 in an up-and-down direction, a right-and-left direction and a rotational direction as illustrated by unlabeled arrows.

Figure 19:
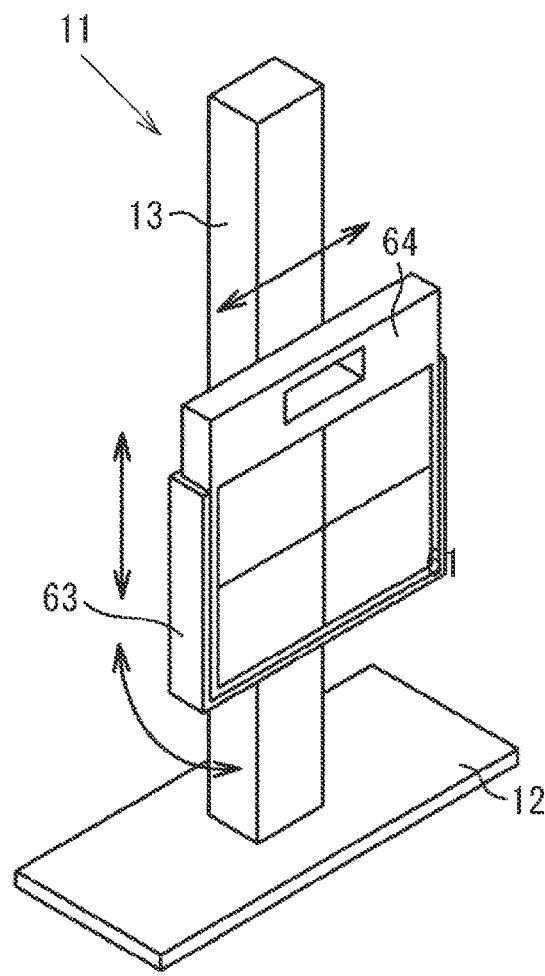
FIG. 19 is a perspective view illustrating a state in which an imaging unit is attached to the pedestal according to the sixth exemplary embodiment.

FIG. 19 is a perspective view of the pedestal 11 illustrating a state in which the base plate 62 is provided with a holder 63 fixed to the base plate 62, and an imaging unit 64 is attached to the holder 63. The holder 63, to which the imaging unit 64 is attached, is configured to be movable in any direction on the plane in parallel with the imaging plane and to be rotatable.

Accordingly, if the imaging unit 64 is rotated by a certain angle and thus the center of the imaging area is shifted from an axis of irradiation of the X-ray, the imaging unit 64 is moved in translation to correct the shifted distance. In this manner, an image including less irradiation unevenness of the X-ray can be obtained. Further, the imaging unit 64 can only be moved in translation without being rotated. As such, photographing other than the general photographing, i.e., a long time photographing or a stereo photographing, can be achieved.

Figure 20:
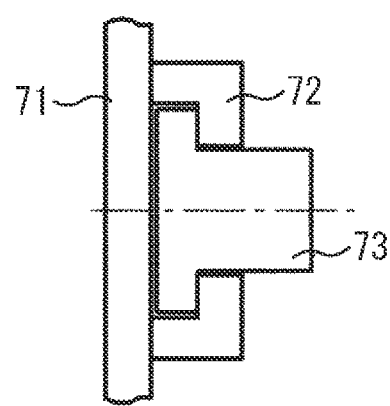
FIG. 20 is a cross sectional view of a holder according to a seventh exemplary embodiment.
Figure 21:
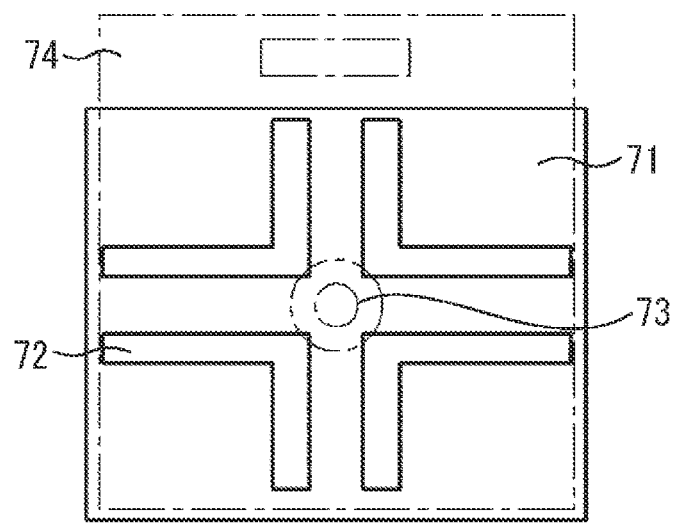
FIG. 21 illustrates a state in which an imaging unit is attached to the holder according to the seventh exemplary embodiment.

FIG. 20 is a cross sectional view of a holder, and FIG. 21 illustrates a state in which an imaging unit is attached to the holder, respectively, according to a seventh exemplary embodiment. Aside of pedestal (not illustrated) of the holder 71 is provided with translation guides 72 combined with a support member 73.

The support member 73 is formed in an axis symmetry shape, so that it can be positioned at predetermined positions on the translation guides 72. With this configuration, an imaging unit 74 can be rotated and translated, as needed.

Since the imaging unit 74 according to the seventh exemplary embodiment can be rotated and moved in translation, if the axis of irradiation of the X-ray is shifted from the center of the imaging area while the imaging unit 74 is rotated, a position of the imaging unit 74 can be fine-adjusted in order to correct the shifted distance.

Figure 22:
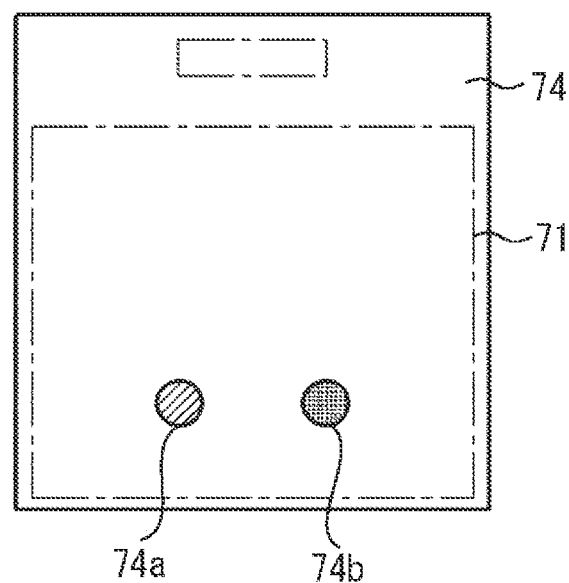
FIG. 22 is a rear elevation of the imaging unit according to the seventh exemplary embodiment.
Figure 23:
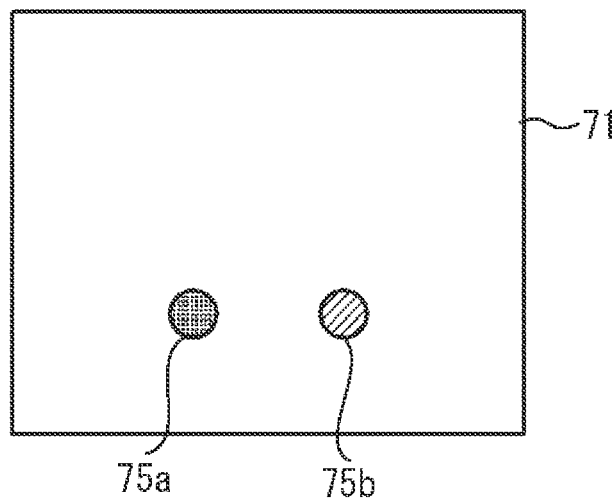
FIG. 23 is a front elevation of the holder according to the seventh exemplary embodiment.

FIG. 22 is a rear elevation of the imaging unit 74 that is provided with point-shaped electrodes 74a and 74b separated by a certain distance. As illustrated in FIG. 23, the holder 71 is formed into one piece with an electrode construction member and is provided with point-shaped electrodes 75a and 75b.

In the seventh exemplary embodiment, positions of the point-shaped electrodes 74a and 74b of the imaging unit 74 would not be shifted from positions of the corresponding point-shaped electrodes 75a and 75b of the holder 71 with each other when the imaging unit 74 is rotated. Accordingly, lowering of the reliability caused by worn electrodes due to repetitive slides, which occurs as a problem when the holder 71 is provided independently from the electrode construction member, can be avoided.

In this case, two point-shaped electrodes may be provided at predetermined positions on the imaging unit 74 and the holder 71, respectively, such that the point-shaped electrodes of the imaging unit 74 and the holder 71 correspondingly mate with each other. Accordingly, a large effect as that shapes of parts can be extremely simplified can be obtained.

Figure 24:
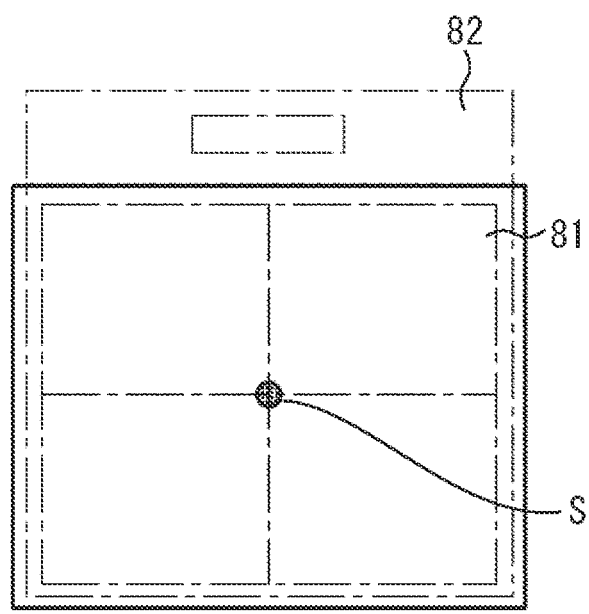
FIG. 24 illustrates a state in which an imaging unit is attached to a holder according to an eighth exemplary embodiment.
Figure 25:
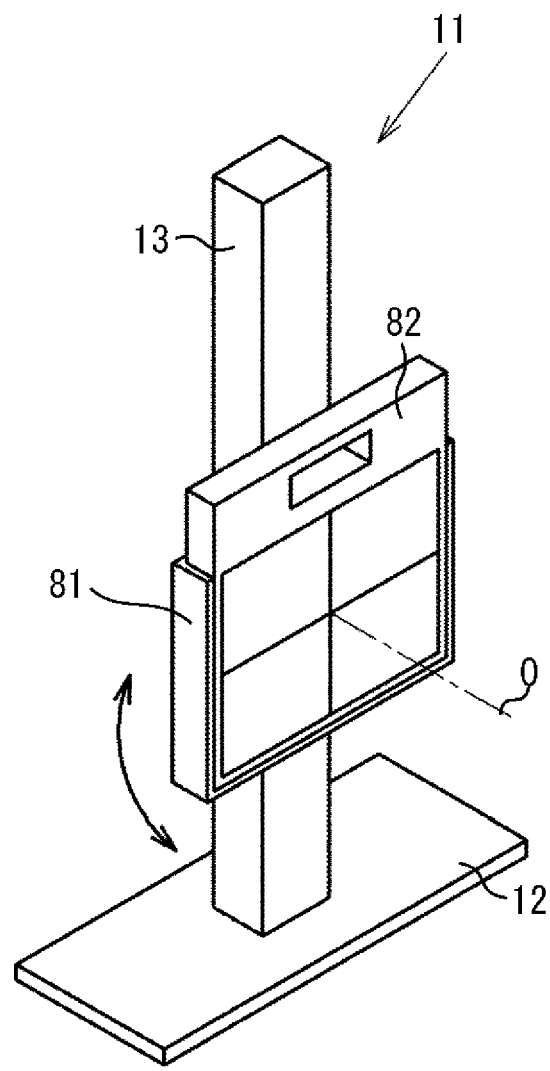
FIG. 25 is a perspective view illustrating a state in which the imaging unit is attached to a pedestal according to the eighth exemplary embodiment.

FIG. 24 illustrates a state in which an imaging unit is attached to a holder 81, and FIG. 25 is a perspective view of the imaging unit and a pedestal, respectively, according to an eighth exemplary embodiment.

At a center "O" of an axis of rotation (FIG. 25), a center of the imaging area coincides with a position of projection of the X-ray. The power feeding mechanism is of a non-contact type in which a contact point is not used but an electromagnetic induction is utilized. Therefore, as long as the X-ray irradiation axis "O" coincides with the center of the imaging area, the imaging unit 82 can be rotated around the X-ray irradiation axis "O" as illustrated in FIG. 25.

Accordingly, a center S (FIG. 24) of the imaging area would not shift due to the rotation of the imaging unit 82, and thus a fine positional adjustment after the rotation is not required, resulting in an operability enhancement in photographing. By proving the holder 81 with a translation mechanism in addition to the rotation mechanism, it is a matter of course that the imaging unit 82 can be moved in translation in addition to the rotation.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed is:

1. An X-ray imaging apparatus, comprising:
    an imaging unit configured to receive electric power via a first power feeding mechanism provided in a back surface opposed to an imaging surface having a photoelectric conversion element for acquiring an X-ray image;
    a pedestal including a second power feeding mechanism configured to feed the electric power to the imaging unit via the first power feeding mechanism;
    a holder disposed on the pedestal and configured to hold the imaging unit so that a position of the first power feeding mechanism coincides with a position of the second power feeding mechanism;
    a moving unit configured to move the holder so that the first power feeding mechanism is moved along with the second power feeding mechanism to an arbitrary position in a plane parallel to the imaging surface of the imaging unit and/or the first power feeding mechanism is rotated by an arbitrary angle with respect to an axis perpendicular to the imaging surface, within a range in which electric power is fed from the second power feeding mechanism to the first power feeding mechanism; and
    a power feeding port configured to feed electric power to the imaging unit via the first and second power feeding mechanisms.

2. The X-ray imaging apparatus according to claim 1,
    wherein the first power feeding mechanism is an electrode having a predetermined shape and the second power feeding mechanism is an electrode having a shape corresponding to the predetermined shape of the first power feeding mechanism, and
    wherein the power feeding port is configured to feed the electric power while the electrodes are in contact with each other.

3. The X-ray imaging apparatus according to claim 2, wherein the holder is movable with respect to the second power feeding mechanism.

4. The X-ray imaging apparatus according to claim 3,
    wherein a position of the second power feeding mechanism in a center of the imaging unit and the holder is not changed when the holder is rotated with respect to the second power feeding mechanism, and
    wherein the first power feeding mechanism or the second power feeding mechanism is formed in a shape according to a track of rotation of the holder or the imaging unit.

5. The X-ray imaging apparatus according to claim 1, wherein a rotation axis of the holder passes through a center of an imaging range of the imaging unit.

6. The X-ray imaging apparatus according to claim 1,
    wherein the power feeding port is of a non-contact type, and
    wherein the power feeding port feeds the electrical power to the imaging unit via the first and second power feeding mechanisms by electromagnetic induction.

7. The X-ray imaging apparatus according to claim 1,
    wherein the first power feeding mechanism includes a point-shaped electrode and a ring-shaped electrode, the ring-shaped electrode being disposed around the point-shaped electrode separated by a first distance, and
    wherein the second power feeding mechanism includes two point-shaped electrodes disposed away from each other by the first distance.

8. The X-ray imaging apparatus according to claim 1,
    wherein the second power feeding mechanism includes a point-shaped electrode and a ring-shaped electrode, the ring-shaped electrode disposed around the point-shaped electrode separated by a predetermined distance, and
    wherein the first power feeding mechanism includes two point-shaped electrodes separated from each other by the predetermined distance.

9. The X-ray imaging apparatus according to claim 1,
    wherein the first power feeding mechanism includes two ring-shaped electrodes having different radii, and
    wherein the second power feeding mechanism includes two point-shaped electrodes corresponding to the radii of the two ring-shaped electrodes.

10. The X-ray imaging apparatus according to claim 1,
    wherein the second power feeding mechanism includes two ring-shaped electrodes having different radii, and
    wherein the first power feeding mechanism includes two point-shaped electrodes corresponding to the radii of the two ring-shaped electrodes.

11. An X-ray imaging apparatus, comprising:
    an imaging unit having an imaging surface and configured to receive electric power via a linear electrode provided on a back surface opposite to the imaging surface;
    a pedestal including a point-shaped electrode, the point-shaped electrode being configured to feed the electric power to the imaging unit via the linear electrode;
    a holder disposed on the pedestal and configured to position and hold the imaging unit so that the linear electrode is in contact with the point-shaped electrode; and
    a moving unit configured to move the holder so that the linear electrode is moved along with the point-shaped electrode to an arbitrary position in a plane parallel to the imaging surface of the imaging unit and/or the linear electrode is rotated by an arbitrary angle with respect to an axis perpendicular to the imaging surface, within a range in which the linear electrode is in contact with the point-shaped electrode.

12. An X-ray imaging system comprising:
    an imaging apparatus having an imaging unit for acquiring an X-ray image via an imaging surface thereof, the imaging apparatus being configured to receive electric power via a first power feeding mechanism provided on a back surface of the imaging unit opposite to the imaging surface;
    a pedestal including a second power feeding mechanism for feeding the electric power to the imaging unit via the first power feeding mechanism;
    a holder disposed on the pedestal and configured to position and hold the imaging unit;
    a moving unit configured to move the holder so that the first power feeding mechanism is moved along with the second power feeding mechanism to an arbitrary position in a plane parallel to the imaging surface of the imaging unit and/or the first power feeding mechanism is rotated by an arbitrary angle with respect to an axis perpendicular to the imaging surface, within a range in which electric power is fed from the second power feeding mechanism to the first power feeding mechanism; and
    a power feeding port configured to feed electric power to the imaging unit via the first and second power feeding mechanisms.

13. An X-ray imaging apparatus comprising:
an imaging unit configured to receive electric power via a first power feeding mechanism provided on a back surface opposed to an imaging surface having a photoelectric conversion element for acquiring an X-ray image;
a second power feeding mechanism configured to feed the electric power to the imaging unit via the first power feeding mechanism;
a holder configured to position and hold the imaging unit; and
a moving unit configured to move the holder so that the first power feeding mechanism is moved along with the second power feeding mechanism to an arbitrary position in a plane parallel to the imaging surface of the imaging unit and/or the first power feeding mechanism is rotated by an arbitrary angle with respect to an axis perpendicular to the imaging surface, within a range in which electric power is fed from the second power feeding mechanism to the first power feeding mechanism.

14. An X-ray imaging apparatus comprising:
an imaging unit configured to receive electric power via a first power feeding mechanism provided on a back surface opposed to an imaging surface having a photoelectric conversion element for acquiring an X-ray image;
a second power feeding mechanism configured to feed the electric power to the imaging unit via the first power feeding mechanism in a non-contact manner;
a holder configured to position and hold the imaging unit; and
a moving unit configured to move the holder so that the first power feeding mechanism is moved along with the second power feeding mechanism to an arbitrary position in a plane parallel to the imaging surface of the imaging unit and/or the first power feeding mechanism is rotated by an arbitrary angle with respect to an axis perpendicular to the imaging surface, within a range in which electric power is fed from the second power feeding mechanism to the first power feeding mechanism.

15. An X-ray imaging apparatus comprising:
an imaging unit having an imaging surface for acquiring an X-ray image, the imaging unit being configured to receive electric power from an external device via a first power feeding mechanism provided on a back surface of the imaging unit opposed to the imaging surface;
a second power feeding mechanism configured to feed the electric power to the imaging unit via the first power feeding mechanism in a non-contact manner; and
a moving unit configured to move the imaging unit so that the first power feeding mechanism is moved along with the second power feeding mechanism to an arbitrary position in a plane parallel to the imaging surface of the imaging unit and/or the first power feeding mechanism is rotated by an arbitrary angle with respect to an axis perpendicular to the imaging surface, within a range in which electric power is fed from the second power feeding mechanism to the first power feeding mechanism.

16. An X-ray imaging apparatus comprising:
an imaging unit having a first mechanism configured to receive electric power;
a second mechanism configured to feed the electric power to the imaging unit via the first mechanism in a non-contact manner; and
a holder configured to hold the imaging unit so that a position of the first mechanism coincides with a position of the second mechanism,
wherein the holder is configured to move the imaging unit so that the first mechanism is moved along with the second mechanism to an arbitrary position in a plane parallel to an imaging surface of the imaging unit and/or the first mechanism is rotated by an arbitrary angle with respect to an axis perpendicular to the imaging surface, within a range in which electric power is fed from the second mechanism to the first mechanism.

17. The X-ray imaging apparatus according to claim 16, wherein the imaging apparatus comprises a battery configured to store the electric power fed from the second mechanism to the first mechanism.

* * * * *